US011451631B2

(12) United States Patent
Hashimoto

(10) Patent No.: US 11,451,631 B2
(45) Date of Patent: Sep. 20, 2022

(54) COMMUNICATION DEVICE, COMMUNICATION SYSTEM, AND COMMUNICATION METHOD

(71) Applicant: TDK CORPORATION, Tokyo (JP)

(72) Inventor: Kazunori Hashimoto, Tokyo (JP)

(73) Assignee: TDK CORPORATION, Tokyo (JP)

(*) Notice: Subject to any disclaimer, the term of this patent is extended or adjusted under 35 U.S.C. 154(b) by 0 days.

(21) Appl. No.: 17/126,259

(22) Filed: Dec. 18, 2020

(65) Prior Publication Data

US 2021/0203724 A1 Jul. 1, 2021

(30) Foreign Application Priority Data

Dec. 26, 2019 (JP) .............................. JP2019-236535

(51) Int. Cl.
*H04L 67/12* (2022.01)
*G16H 80/00* (2018.01)
*H04L 67/131* (2022.01)
*H04L 67/125* (2022.01)

(52) U.S. Cl.
CPC ............. *H04L 67/12* (2013.01); *G16H 80/00* (2018.01); *H04L 67/125* (2013.01); *H04L 67/131* (2022.05)

(58) Field of Classification Search
CPC ...... H04L 67/12; H04L 67/125; H04L 67/131
USPC ....................................................... 709/201
See application file for complete search history.

(56) References Cited

U.S. PATENT DOCUMENTS

| | | | | |
|---|---|---|---|---|
| 2009/0119360 | A1* | 5/2009 | Robinson | G16H 40/67 709/203 |
| 2014/0240122 | A1* | 8/2014 | Roberts | A61B 5/7455 340/539.11 |
| 2018/0293568 | A1* | 10/2018 | Gurunathan | G06Q 20/36 |
| 2020/0275394 | A1* | 8/2020 | Lam | H04W 56/001 |
| 2021/0133664 | A1* | 5/2021 | Perez | G06Q 10/083 |
| 2021/0377820 | A1* | 12/2021 | Iida | H04W 36/0055 |
| 2021/0385044 | A1* | 12/2021 | Scholten | H04W 88/04 |

FOREIGN PATENT DOCUMENTS

| | | | | |
|---|---|---|---|---|
| EP | 1833269 A1 * | 9/2007 | | G16H 40/67 |
| JP | 2009-260451 A | 11/2009 | | |

* cited by examiner

*Primary Examiner* — Tauqir Hussain
(74) *Attorney, Agent, or Firm* — Oliff PLC

(57) ABSTRACT

A communication device includes a first communication circuit configured to receive, from a user terminal, a notification signal including at least identification information and request information representing a transmission request to provide transmission data including at least biomedical information, a second communication circuit configured to receive the transmission data from the user terminal, and a controller. The controller executes, in parallel, a first process including receiving the notification signal from the user terminals by controlling the first communication circuit and a second process including receiving the transmission data from the user terminal among the user terminals by controlling the second communication circuit, and determines to receive the transmission data from the user terminal, among the user terminals, when the request information in the notification signal received from the user terminal represents that the biomedical information to be transmitted is recorded in the user terminal.

19 Claims, 13 Drawing Sheets

*Fig.6*

| .. | ID | .. | SOS FLAG | UPLOAD REQUEST FLAG | CONNECTION FLAG | .. |

Fig.10

| NUMBER | IDENTIFICATION INFORMATION ID | .. |
|--------|-------------------------------|-----|
| 1 | ID1 | .. |
| 2 | ID2 | .. |
| . . | . . | . . |

COMMUNICATION DEVICE, COMMUNICATION SYSTEM, AND COMMUNICATION METHOD

CROSS-REFERENCE TO RELATED APPLICATIONS

This application claims the priority under 35 U.S.C. § 119 of JP Patent Application No. 2019-236535, filed on Dec. 26, 2019; the contents of which are relied upon and incorporated herein by reference in its/their entirety.

TECHNICAL FIELD

One aspect of embodiments relates to a communication device, a communication system, and a communication method.

BACKGROUND

Gateway devices collecting data from terminal devices such as a plurality of sensor nodes are developed (see Patent Document 1: Japanese Unexamined Patent Publication No. 2009-260451). For example, a gateway device disclosed in the Patent Document 1 includes a plurality of radio communication units. A sensor node selects a path having a satisfactory communication quality to connect and transmit data to the Gateway device, among paths reaching the radio communication units of the Gateway device.

In the data communication technology disclosed in Patent Document 1, when data is collected from a plurality of terminal devices, communications between terminal devices and the gateway device may cause a collision. For this reason, in some cases, data cannot be efficiently collected from a plurality of terminal devices. For example, such an inefficient data transmission could affect collection of data (for example, biomedical information or the like) that tends to be continuously generated in each of a plurality of terminal devices.

One object of the embodiment is to provide a communication device, a communication system, or a communication method capable of efficiently collecting data from terminal devices.

SUMMARY

A communication device according to one form of this embodiment includes: a first communication circuit configured to receive, from a user terminal among one or more user terminals including the user terminal, a notification signal including at least identification information to identify the user terminal and request information representing a transmission request to provide transmission data including at least biomedical information relating to a user of the user terminal;

a second communication circuit configured to receive the transmission data from the user terminal; and a controller configured to execute, in parallel, a first process including receiving the notification signal from the one or more user terminals by controlling the first communication circuit and a second process including receiving the transmission data from the user terminal among the one or more user terminals by controlling the second communication circuit, and determine to receive the transmission data from the user terminal, among the one or more user terminals, when the request information in the notification signal received from the user terminal represents that the biomedical information to be transmitted is recorded in the user terminal.

A communication method according to another form is a communication method executed by a communication device and includes: executing a first process of receiving a notification signal from one or more user terminals and a second process of receiving a transmission data from a user terminal among the one or more user terminals in parallel, the notification signal including at least identification information to identify the user terminal and request information representing transmission request to provide the transmission data, the transmission data including at least biomedical information relating to a user of the user terminal; and determining to receive the transmission data from the user terminal among the one or more user terminals, when the request information in the notification signal received from the user terminal represents that the biomedical information to be transmitted is recorded in the user terminal.

A communication system according to another form includes: the communication device described above; and the one or more the user terminals.

According to the communication device, data can be efficiently collected from a user terminal which includes biomedical information to be collected, among one or more user terminals that have transmitted a notification signal.

BRIEF DESCRIPTION OF THE DRAWINGS

FIG. 6 illustrates one example of a data format of a notification communication packet transmitted by the terminal device 1.

FIG. 10 is a diagram illustrating one example of the data configuration of transmission management data recorded by the gateway device 2 according to the embodiment.

DETAILED DESCRIPTION

An embodiment will be described with reference to the accompanying drawings. When applicable, the same reference signs will be assigned to the same parts, and duplicate description will be omitted.

Figure 1:
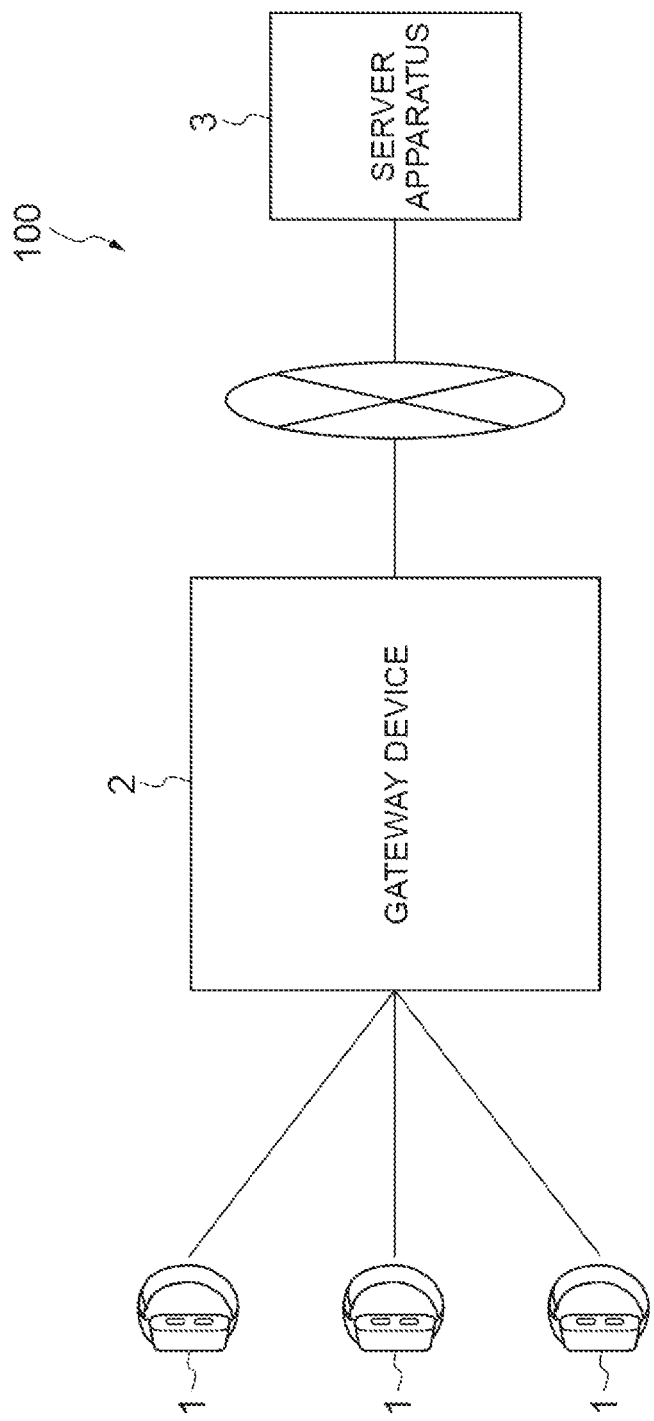
FIG. 1 is a configuration diagram of a communication system 100 according to an embodiment.

FIG. 1 illustrates the configuration of a communication system 100 according to this embodiment. The communication system 100 includes one or more devices that collect a user's biomedical information. The system 100 illustrated in FIG. 1 includes a terminal device 1 that is a user terminal used by a user, a gateway device 2 that are communication devices, and a server apparatus 3 that manages biomedical information. A plurality of gateway device 2 may be included in the system 100. A plurality of terminal devices 1 may be included in the system 100.

Figure 2:
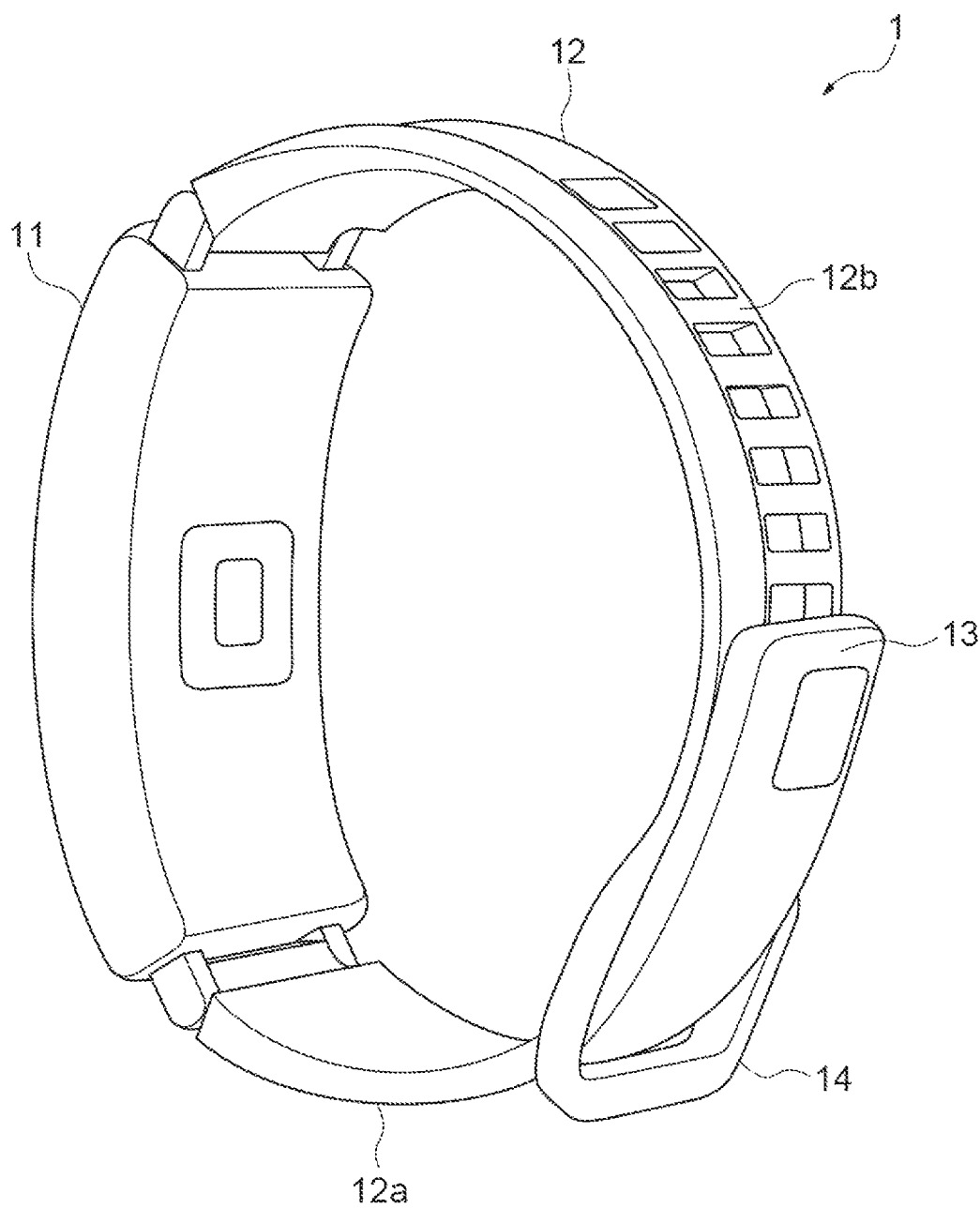
FIG. 2 is an external view of a terminal device 1 according to an embodiment.

FIG. 2 is an external view illustrating one form of the terminal device 1 according to this embodiment. The terminal device 1 is configured to include a main body unit 11 and a mounting unit 12. As one example, the terminal device 1 is a wrist band-type wearable device that worn around the wrist of a target person (user wearing the device) whose biomedical information and the like (described below) is measured. The form illustrated in FIG. 2 is one example that is able to realize the terminal device 1. The terminal device 1, for example, is able to employ an appropriate form according to user's wearing part (part of the body) or the like.

The mounting unit 12 includes two bands 12a and 12b mounted at both ends of the main body unit 11 in the longitudinal direction. The two bands 12a and 12b are formed in a long narrow band shape and respectively have clasps 13 and 14 at tip ends thereof. The mounting unit 12 is worn around a user's forearm (wrist) such that the two bands 12a and 12b wind around the user's forearm. A user put the main body unit 11 on an outer side of the forearm (a back side of the hand), winds the two bands 12a and 12b to the inner side of the forearm (the palm side), and locks the clasps 13 and 14, thereby wearing the terminal device.

Although not illustrated in FIG. 2, operation buttons and a display may be disposed as user interfaces in the terminal device 1.

Figure 3:
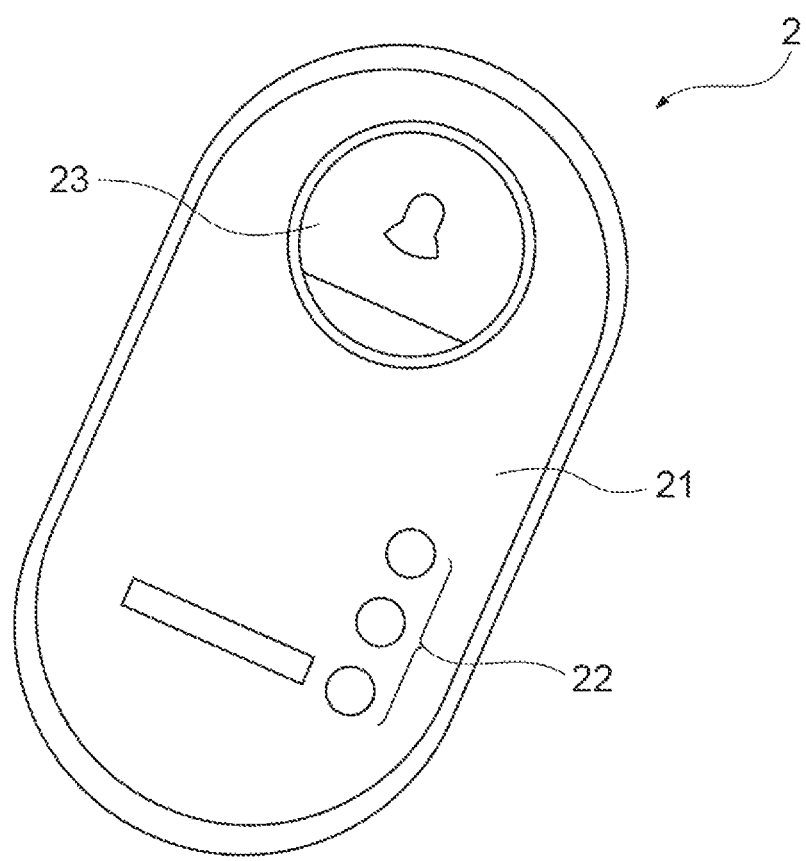
FIG. 3 is an external view of a gateway device 2 according to an embodiment.

FIG. 3 is an external view illustrating one form of the gateway device 2 according to this embodiment. The gateway device 2 is a communication device that is configured to communicate with the terminal device 1. The gateway device 2 may be a stationary-type communication device that may be installed at a specific place or a portable-type communication device.

As an example embodiment illustrated in FIG. 3, a display lamp unit 22 including a light emitting diode (LED) and an operation button 23 are disposed in the main body unit 21 of the gateway device 2. For example, the gateway device 2, as illustrated in FIG. 3, may be formed in an approximately oval shape.

The gateway device 2 may be installed in an area of one or more buildings or the like, where a user wearing the terminal device 1 perform a variety of activities. For example, a plurality of gateway devices 2 may be installed within an area where a user acts inside, such as a private house, an apartment house, a hospital, an aged care facility, and the like.

Figure 4:
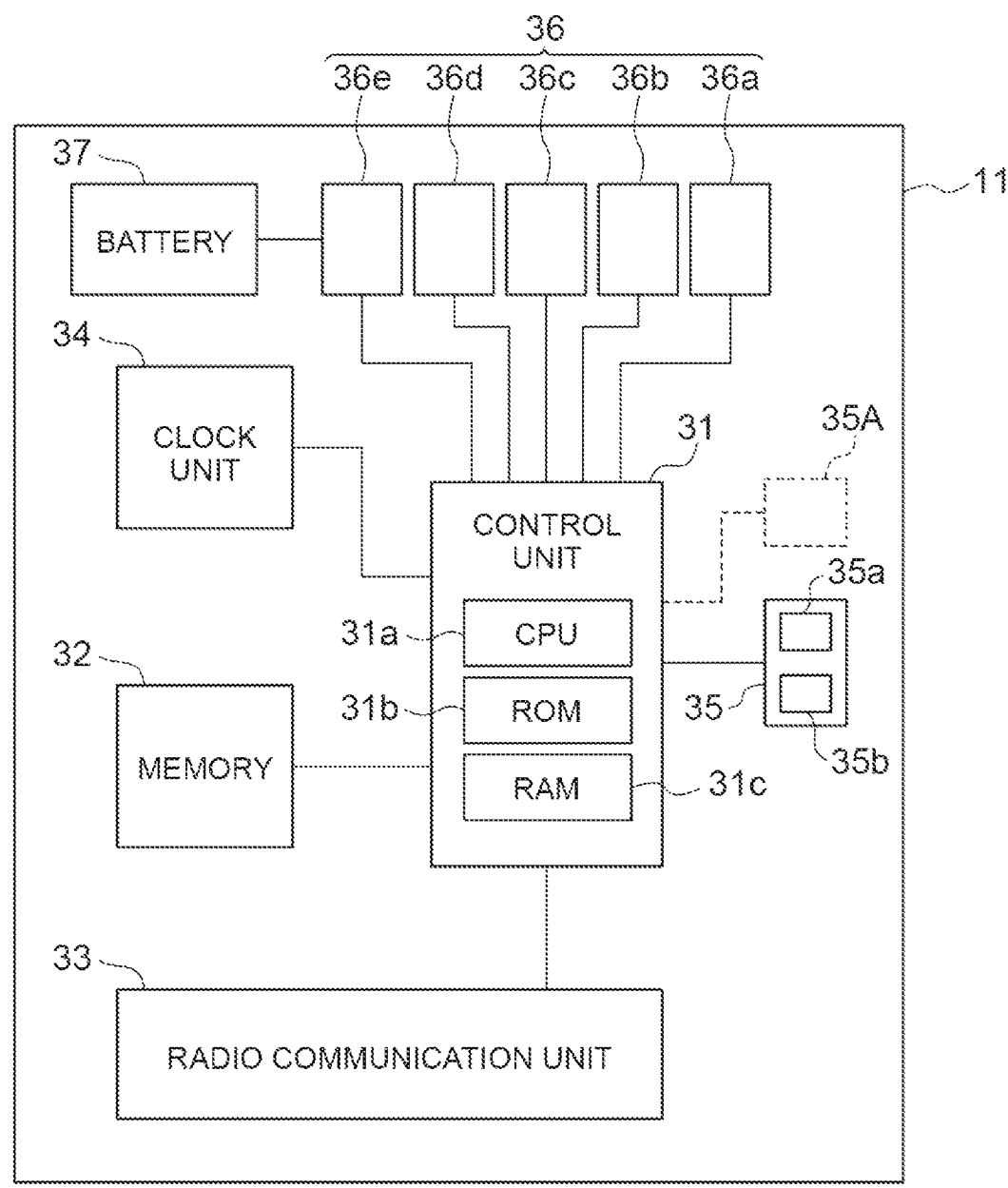
FIG. 4 is a block diagram illustrating the hardware configuration of a main body unit 11 of the terminal device 1 according to the embodiment.

FIG. 4 is a block diagram illustrating the hardware configuration of a main body unit 11 of the terminal device 1 according to this embodiment. The main body unit 11 of the terminal device 1 includes a control unit 31, a memory 32, a radio communication unit 33, a clock unit 34, an operation display unit 35 as a user interface, a sensor unit 36 including various sensors, and a battery 37.

The control unit 31 includes a central processing unit (CPU) 31a, a read only memory (ROM) 31b, a random access memory (RAM) 31c, and various interfaces (hereinafter, simply abbreviated as interface) not illustrated in the drawing.

The ROM 31b of the control unit 31 is a storage device that is able to store, for example, various data and software programs and the like that enables to realize various functions and operations of the terminal device 1. For example, a function of calculating useful data from output signals of various sensors and the like, a communication function of transmitting the calculated data to the gateway device 2, and the like may be included in the various functions implemented by the software programs. The ROM 31b may be a rewritable nonvolatile memory such as a flash memory.

The memory 32 is a storage device that stores at least data detected by various sensors. For example, the memory 32 may also be a rewritable nonvolatile memory such as a flash memory.

The radio communication unit 33 is circuitry that enables radio communication with the gateway device 2 which is placed within a certain distance. A communication distance to enable radio communication for the radio communication unit 33 may be appropriately set in accordance with standards, specifications and the like. For example, the communication distance for the radio communication unit 33 may be equal to or shorter than 100 m.

In this embodiment, the radio communication unit 33 may include a circuit that enables near field communication. In such case, for example, the radio communication unit 33 may be controlled by the control unit 31 and perform near field communication with the gateway device 2. More specifically, in this embodiment, the radio communication unit 33 may include a circuit that is used for radio communication, for example, according to the Bluetooth (registered trademark) standards. In such a case, the terminal device 1 and the gateway device 2 are communicatively connected to each other using near field communication according to the Bluetooth (registered trademark) standards.

The clock unit 34 is a circuit that generates and outputs time information. An output signal including the time information of the clock unit 34 is provided to the control unit 31 through an interface not illustrated in the drawing, and a CPU 31a is able to obtain the time information, for example, including year/month/date and a time from the clock unit 34. In addition, the clock unit 34 may provide an elapsed time (or a clock count) from a specific timing as the time information. As will be described below, measurement data obtained by the sensor unit 36 may be stored in the memory 32 together with the time information of the clock unit 34 and transmitted to the gateway device 2.

The operation display unit 35 includes a display 35a such as a light emitting diode (LED) and an operation button 35b that is a component to detect a user's operation. An operation detected by the operation button 35b is provided to the control unit 31 through an interface not illustrated in the drawing. The display 35a and the operation button 35b of the operation display unit 35, for example, may be implemented as a display device with an attached touch panel.

The sensor unit 36 includes a plurality of sensors and a measurement circuitry. The sensor unit 36 may include an acceleration sensor 36a, a temperature sensor 36b, a pulse wave sensor 36c, an ultraviolet sensor 36d, and a battery voltage measuring circuit 36e.

The acceleration sensor 36a, for example, is a sensor that is configured to measure accelerations of one or more axes. The acceleration sensor 36a according to this embodiment, for example, may be a sensor that detects accelerations in three axial directions (which are orthogonal to each other). By detecting a motion of a user's arm wearing the terminal device 1, the acceleration sensor 36a enables to count the number of steps and calculates consumed calories of the user, as biomedical information acquired by sensing a user's body.

The temperature sensor 36b is a sensor that is able to detect a temperature. In this embodiment, the temperature sensor 36b, for example, may be a temperature sensor that is configured to detect a body surface temperature of a user wearing the terminal device 1 as biomedical information. The temperature sensor 36b is disposed at a position in the main body unit 11 at which the temperature of the arm can be detected when the terminal device 1 is worn on the user's arm.

The pulse wave sensor 36c is a sensor that is able to detect a pulse of a user wearing the terminal device 1. In this embodiment, the pulse wave sensor 36c, for example, is able to detect a pulse of a user as biomedical information. The pulse wave sensor 36c is also disposed at a position in the main body unit 11 at which a pulse wave of a user can be detected when the terminal device 1 is worn on the user's arm. The pulse wave sensor 36c, for example, may be implemented by use of, an optical sensor, a piezoelectric element that can detect a pressure pulse wave, or an acoustic sensor that can detect a pulse sound.

The ultraviolet sensor 36d is a sensor that is able to detect the amount of ultraviolet rays. The ultraviolet sensor 36d, for example, may be configured to detect the amount of ultraviolet rays reaching the terminal device 1. The ultraviolet sensor 36d is disposed at a position in the main body unit 11 at which ultraviolet rays from the outside can be detected, when the terminal device 1 is worn on the user's arm. For example, an introduction part (for example, an opening, a transmission window, or the like) may be disposed in the main body unit 11. The introduction part is configured to allow light rays to reach to a position at which the ultraviolet rays can be detected by the ultraviolet sensor 36d.

The battery voltage measuring circuit 36e is a circuit that is connected to the battery 37 and able to measure an output voltage of the battery 37.

An output signal of each sensor in the sensor unit 36 is input to the control unit 31 through an interface not illustrated in the drawing. An output signal of the battery voltage measuring circuit 36e is also provided to the control unit 31 through an interface not illustrated in the drawing.

The battery 37 may include, for example, a secondary battery or the like and. The battery 37 provides power source that supplies electric power to various circuits of the terminal device 1.

Figure 5:
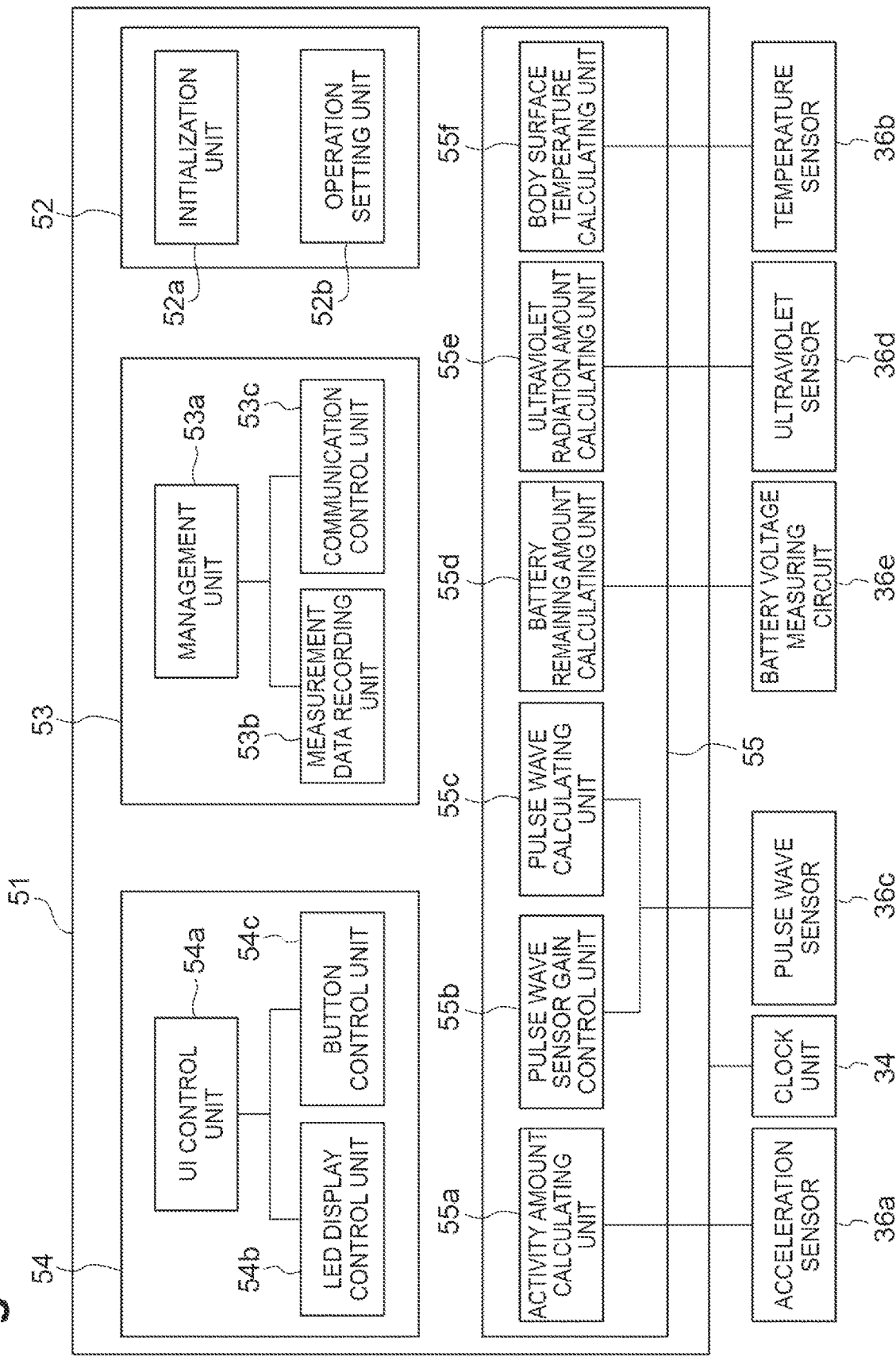
FIG. 5 is a block diagram illustrating a functional configuration of the terminal device 1 according to the embodiment.

FIG. 5 is a block diagram illustrating configuration of the software program enables to realize various functions of the terminal device 1.

As illustrated in FIG. 5, software 51 of the terminal device 1 includes a control integration unit 52 that controls the overall operation of the terminal device 1, a data providing unit 53, a user interface (hereinafter, abbreviated to a UI) unit 54, and a data measuring unit 55. The control integration unit 52, the data providing unit 53, the UI unit 54, and the data measuring unit 55 may be implemented as software programs and stored in the ROM 31b. For example, functions of the terminal may be realized by the CPU 31a reading such programs from the ROM 31b and executing the programs.

An output signal of each sensor of the sensor unit 36 is provided to the control unit 31 and is converted into digital data. An output signal of the battery voltage measuring circuit 36e and an output signal of the clock unit 34 are also provided to the control unit 31 and are converted into digital data.

The control integration unit 52 may include an initialization unit 52a and an operation setting unit 52b. The initialization unit 52a may be implemented as a program to perform initialization of the terminal device 1 when the terminal device 1 is turned on. The operation setting unit 52b may be implemented as a program to perform settings relating to various operations for executing various processes in accordance with an operation state of the terminal device 1. With these configurations, the control integration unit 52 is able to control an overall operation of the terminal device 1.

The data providing unit 53 may include a management unit 53a, a measurement data recording unit 53b, and a communication control unit 53c.

The management unit 53a manages control process to record data and a communication in the data providing unit 53. More specifically, the management unit 53a controls operations of the measurement data recording unit 53b and the communication control unit 53c, according to direction by the control integration unit 52.

The measurement data recording unit 53b performs the process of recording, in the memory 32, measurement data provided by each sensor of the sensor unit 36. The communication control unit 53c performs a control process for performing radio communication with the gateway device 2 using the radio communication unit 33. For example, the communication control unit 53c controls near field communication according to Bluetooth (registered trademark) communication standards. In other words, when a transmission request is received from the gateway device 2 through near field communication, the communication control unit 53c controls to transmit measurement data as transmission data to the gateway device 2, by including biomedical information stored in the memory 32 into the transmission data, and using radio communication.

In addition, the communication control unit 53c may implement function of notifying the gateway device 2 of its presence (the terminal device 1's presence) by controlling the radio communication unit 33. In this embodiment, as one example, the communication control unit 53c may perform a process of notifying another Bluetooth (registered trademark) device within a radio communication range of its presence by transmitting a Bluetooth (registered trademark) low energy communication standards advertising packet (Bluetooth (registered trademark) standards of 4.0 or later).

An advertising packet is a signal defined in the Bluetooth (registered trademark) communication standards and can be used as presence notification. Advertising packets are intermittently transmitted using a broadcast system. In other words, an advertising packet can be used as a beacon signal. The terminal device 1, for example, may transmit an advertising packet as a presence notification signal intermittently (for example, at intervals of two seconds) through radio communication using a broadcast system.

FIG. 6 illustrates one example of a data format of a notification communication packet (notification signal) transmitted with this advertising packet. As illustrated in FIG. 6, for example, a notification communication packet including an advertising packet may include an identification information ID (hereinafter simply abbreviated as ID), an SOS flag, an upload request flag (request information), and a connection flag.

The ID represents information identifying a terminal device 1 as a transmission source of the advertising packet. The ID, for example, may be a combination of a number, a character, a symbol, and the like that is able to uniquely identify a terminal device 1.

The SOS flag is information that represents a degree of urgency according to an operation detected by a button control unit 54c. For example, the degree of urgency may be represented by use of a numerical value or binary data (0 or 1) in the SOS flag.

The upload request flag (request information) represents a request for uploading (receiving by the gateway device 2) transmission data to the gateway device 2. More specifically, for example, the upload request flag may represent whether the terminal device 1 has the request for uploading transmission data to gateway device 2 or not. The upload request flag, for example, may represent an upload request using a numerical value or may represent an upload request as binary data (0 or 1).

The connection flag, for example, represents whether or not a data communication function of the radio communication unit 33 is occupied due to transmission data being transmitted in the terminal device 1. The connection flag, for example, may represent an occupancy state of the data communication function of the radio communication unit 33 using a numerical value or may represent the occupancy state as binary data (0 or 1).

As a specific example, the ID, for example, may be a MAC address of the terminal device 1 and may be set in a packet header of a notification communication packet. The SOS flag may be set to "on" (for example, "1") or "off" (for example, "0") in accordance with an SOS signal detected by the button control unit 54c. The upload request flag may be set to "on" or "off" in accordance with whether measurement data which has not been transmitted are stored in the memory 32 (or whether the measurement data stored in the memory 32 have reached certain data amount). The connection flag may be set to "on" or "off" in accordance with a control state according to the communication control unit 53c.

Referring back to FIG. 5, the UI unit 54 includes a UI control unit 54a, an LED display control unit 54b, and a button control unit 54c. The UI control unit 54a performs a process relating to the operation display unit 35. The UI control unit 54a controls the LED display control unit 54b and the button control unit 54c. In other words, the UI control unit 54a controls operations of the LED display control unit 54b and the button control unit 54c under direction of the control integration unit 52.

The LED display control unit 54b performs control of changing a display state of the display 35a in accordance with an instruction from the UI control unit 54a.

The button control unit 54c detects a user's operation performed on the operation button 35b and provides operation information to the UI control unit 54a. For example, when a user's operation notifying urgent situation (the degree of urgency is high) is detected, the button control unit 54c provides an SOS signal to the UI control unit 54a. The SOS signal is not limited to be generated in accordance with detection of the user's operation. The SOS signal may be generated by the data measuring unit 55 (described below) based on a degree of urgency calculated in accordance with an output signal from the sensor unit 36.

The data measuring unit 55 includes an activity amount calculating unit 55a, a pulse wave sensor gain control unit 55b, a pulse wave calculating unit 55c, a battery remaining amount calculating unit 55d, an ultraviolet radiation amount calculating unit 55e, and a body surface temperature calculating unit 55f. Measurement data measured by the data measuring unit 55 are recorded in the memory 32 by the measurement data recording unit 53b.

The activity amount calculating unit 55a calculates the number of steps and burned calories of a user on the basis of an output signal of the acceleration sensor 36a as biomedical information. The pulse wave sensor gain control unit 55b, for example, can control a gain of the pulse wave sensor 36c.

The pulse wave calculating unit 55c calculates a pulse on the basis of an output signal of the pulse wave sensor 36c, as biomedical information. The battery remaining amount calculating unit 55d, for example, calculates a battery remaining amount of the battery 37 on the basis of data of an output voltage of the battery 37. The battery voltage measuring circuit 36e measures the output voltage of the battery 37.

The ultraviolet radiation amount calculating unit 55e calculates the amount of ultraviolet rays on the basis of an output signal of the ultraviolet sensor 36d. The body surface temperature calculating unit 55f calculates a user's body surface temperature on the basis of an output signal of the temperature sensor 36b as biomedical information.

As described above, the data measuring unit 55 calculates measurement data including biomedical information on the basis of output signals from appropriate sensors and control circuits.

Figure 7:
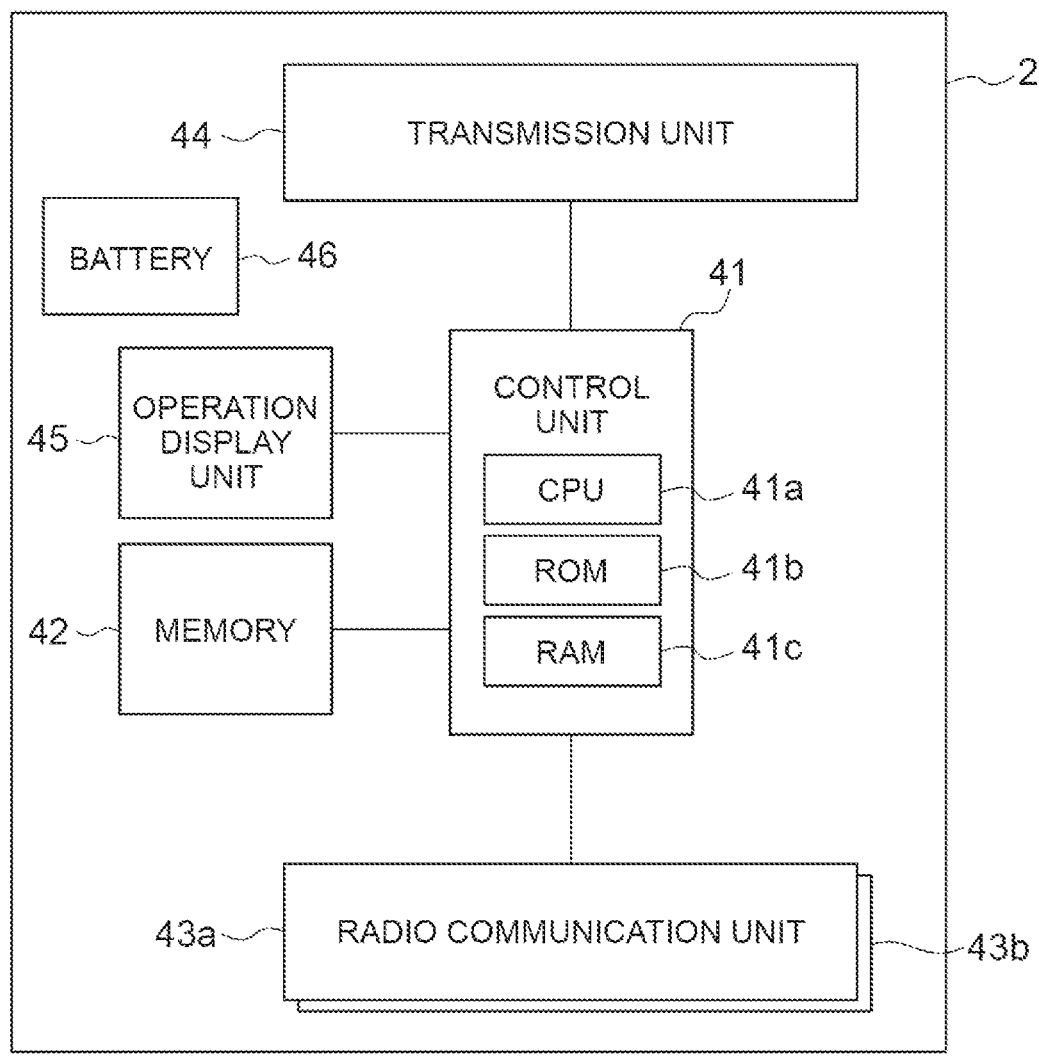
FIG. 7 is a block diagram illustrating the hardware configuration of the gateway device 2 according to the embodiment.

FIG. 7 is a block diagram illustrating the hardware configuration of the gateway device 2 according to this embodiment. The gateway device 2 includes a control unit 41, a memory 42, radio communication units 43a and 43b, a transmission unit 44, an operation display unit 45 as a user interface, and a battery 46.

The control unit 41 includes a CPU 41a, a ROM 41b, a RAM 41c, and various interfaces not illustrated in the drawing.

Software programs, data, and the like that implement various functions of the gateway device 2 are stored in the ROM 41b of the control unit 41. For example, functions such as communication with the terminal device 1, communication with the server apparatus 3, and the like may be implemented in the various functions. The ROM 41b may be a rewritable nonvolatile memory such as a flash memory.

The memory 42 is a storage device that can store various kinds of information for communication. The memory 42, for example, may be a rewritable nonvolatile memory such as a flash memory. Data from the terminal device 1 is stored in the memory 42 or the RANI 41c.

Each of the radio communication units 43a and 43b is a circuit that enables radio communication for communicating with the terminal device 1 within certain distance. The radio communication units 43a and 43b may include a circuit that is used for radio communication according to the Bluetooth (registered trademark) standards. The radio communication units 43a and 43b performs radio communication with the terminal device 1 under direction of the control unit 41. The gateway device 2 may receive a notification communication packet including the advertising packet described above from the terminal device 1, by performing Bluetooth (registered trademark) communication using the radio communication unit 43a. In addition, the gateway device 2 may also receive the transmission data described above from the terminal device 1 by performing Bluetooth (registered trademark) communication using the radio communication unit 43b. In accordance with such a configuration, the gateway device 2 is configured to receive a notification communication packet and reception of transmission data in parallel (simultaneously) with each other.

The transmission unit 44 is a circuit realizes data communication with the server apparatus 3 to be described below through wired communication, wireless communication, or a combination thereof. The transmission unit 44, for example, may be a circuit that is configured for radio communication of a cellular system used for a mobile phone and the like, or may be a circuit that is configured for local communication such as a wireless local area network (LAN) or a wired LAN. The transmission unit 44 performs communication with the server apparatus 3 under direction of the control unit 41. In a case in which a wireless communication system is employed as a communication system for communicating with the server apparatus 3, for example, the transmission unit 44 may include a circuit that enables connection to the Internet through a close wireless base station and communicates with the server apparatus 3.

The gateway device 2 transmits user data including ID included in a notification communication packet received from the terminal device 1 to the server apparatus 3, through data communication using the transmission unit 44. The gateway device 2 also transmits transmission data that has been received from the terminal device 1 through the data communication to the server apparatus 3.

The operation display unit 45 includes a display lamp unit 22 and an operation button 23 operated by a user as illustrated in FIG. 2. The battery 46, for example, is a secondary battery or the like and is a power source that supplies electric power to various circuits of the gateway device 2.

Figure 8:
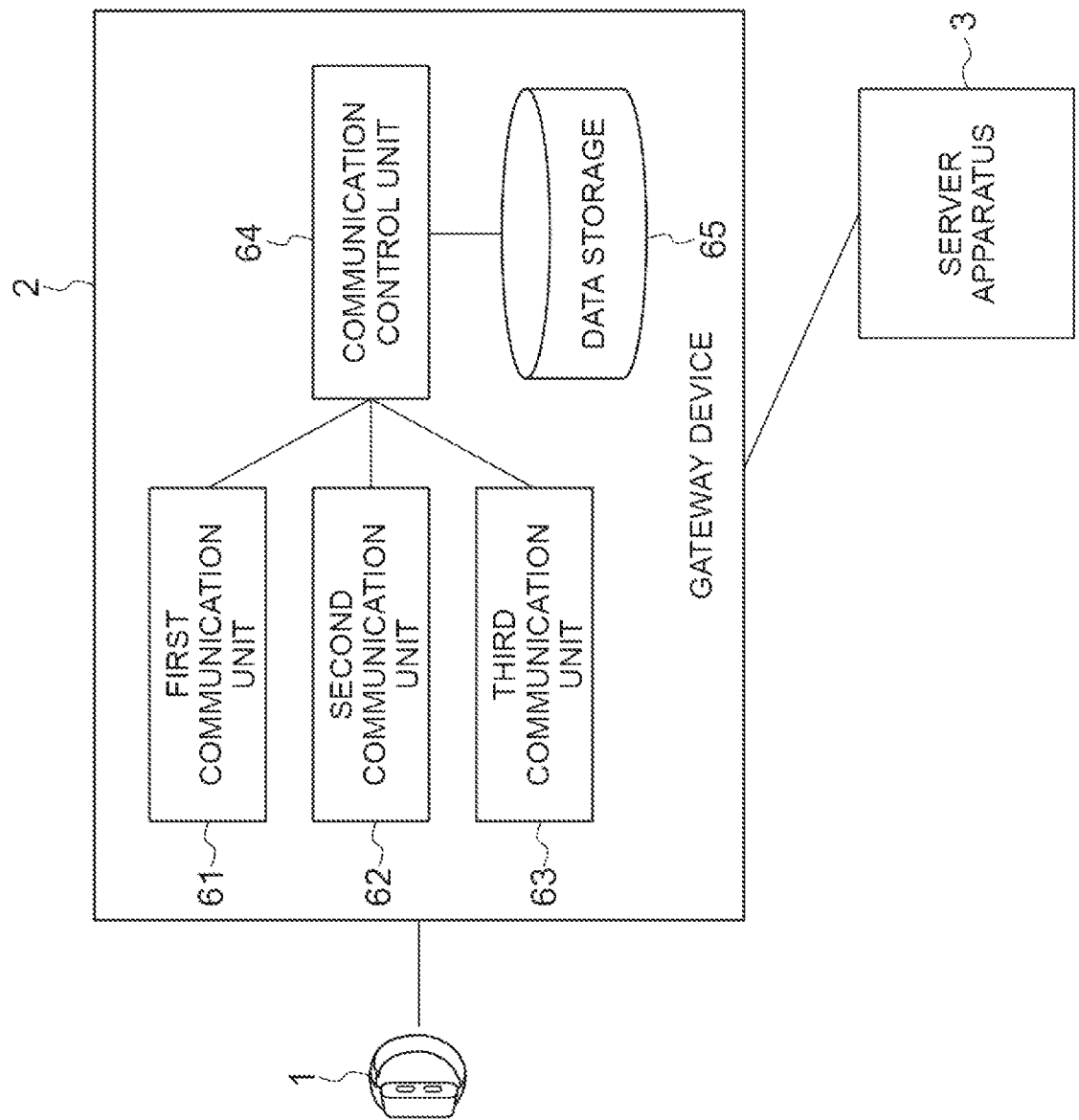
FIG. 8 is a block diagram illustrating a functional configuration of the gateway device 2 according to the embodiment.
Figure 9:
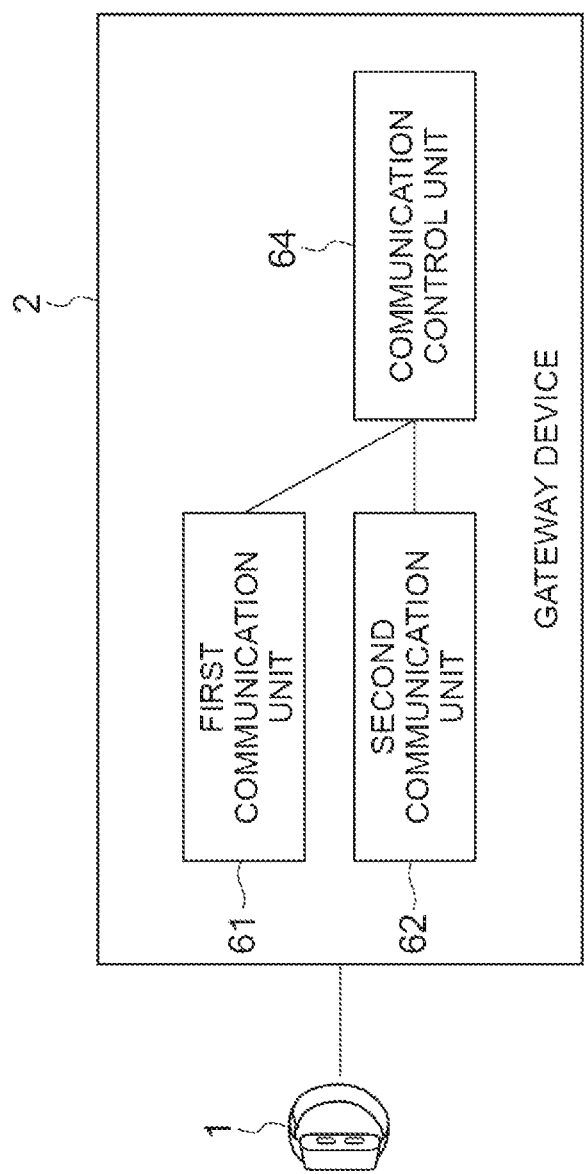
FIG. 9 is a block diagram illustrating another functional configuration of the gateway device 2 according to the embodiment.

The functional configuration of the gateway device 2 will be described with reference to FIGS. 8 and 9. FIG. 9 is a block diagram illustrating one functional configuration of the gateway device 2. FIG. 9 is block diagram illustrating another functional configuration of the gateway device 2. The gateway device 2 according to this embodiment may be realized using the configuration illustrated in FIG. 8 or the configuration illustrated in FIG. 9. The functional configurations of the gateway device 2 illustrated in FIGS. 8 and 9, for example, are realized by the CPU 41a reading and executing a software program stored in the ROM 41b.

As illustrated in FIG. 9, the gateway device 2 includes a first communication unit (first communication circuit) 61, a second communication unit (second communication circuit) 62, and a communication control unit 64. In case of employing the configuration illustrated in FIG. 8, the gateway device 2 may further include a third communication unit (third communication circuit) 63 and a data storage 65. The data storage 65 is a storage device that is configured to store data used for various processes using the first communication unit 61, the second communication unit 62, the third communication unit 63, and the communication control unit 64, and data acquired through various processes.

The configuration of the gateway device 2 illustrated in FIG. 8 will be described as a specific example of this embodiment. In a case in which the configuration illustrated in FIG. 9 is employed, the gateway device 2 may store data (for example, a notification communication packet, transmission data, and the like) received from the terminal device 1 in its own device or may appropriately transmit the data to another communication device using an appropriate method.

The first communication unit 61 is communicatively connected to the terminal device 1 through radio communication by operating the communication function of the radio communication unit 43a. The first communication unit 61 searches for one or more terminal devices 1 exist within a radio communication range by receiving notification communication packets from terminal devices 1 through radio communication. The first communication unit 61 acquires the ID included in notification communication packets received from each of the terminal devices 1. The first communication unit 61 acquires radio wave intensities (signal intensities) of radio communication when notification communication packets are received through radio communication. Then, the first communication unit 61 provides the ID and the information of radio wave intensities for the communication control unit 64.

The second communication unit 62 is communicatively connected to the terminal device 1 through radio communication by operating the communication function of the radio communication unit 43b. The second communication unit 62 transmits a transmission request to the terminal device 1 through radio communication and receives transmission data from the terminal device 1 in response thereto. At this time, the second communication unit 62 transmits the transmission request to the terminal device 1 when a communication connection of radio communication is established after the gateway device 2 requests the terminal device 1 to enable the connection. The second communication unit 62 may set a specific size of transmission data received at one time for each of a plurality of terminal devices 1. The size of this transmission data may be larger than the size of data included in a notification communication packet.

The third communication unit 63 transmits user data and transmission data to the server apparatus 3 by operating the communication function of the transmission unit 44. The third communication unit 63 may load the user data and the transmission data from the data storage 65.

The communication control unit 64 controls operations of the first communication unit 61 and the second communication unit 62. The communication control unit 64 may further control the operation of the third communication unit 63. More specifically, the communication control unit 64 executes receiving process of a notification communication packet (first reception process) using the first communication unit 61 and receiving process of a transmission data (second reception process) using the second communication unit 62, in parallel with each other. Hereinafter, details of control of the first and second reception processes using the communication control unit 64 will be described.

The communication control unit 64 controls the first communication unit 61 to periodically wait for a notification communication packet in a scanning period (for example, certain duration of time longer than or equal to 10 seconds and shorter or equal to 20 seconds). The scanning period is a duration set for receiving a notification communication packet. In this way, the first communication unit 61 searches for a plurality of terminal devices 1. This scanning period may be set in advance to be longer than a transmission interval (for example, an interval of two seconds) of a notification communication packet in the terminal device 1. The communication control unit 64 may not detect a notification communication packet from the terminal device 1 that has been retrieved once within the scanning period. The communication control unit 64 may generate positional data representing a relative position between the terminal device 1 and the gateway device 2, by estimating a positional relation between the terminal device 1 and the gateway device 2 in accordance with a radio wave intensity acquired by the first communication unit 61. The positional data, for example, may represent an area in which the terminal device 1 exists. For example, the communication control unit 64 may estimate a distance between the terminal device 1 and the gateway device 2 by comparing the radio wave intensity with a plurality of thresholds set in advance, and thereby generate the data representing the area where the terminal 1 exists.

The communication control unit 64 stores user data in the data storage 65, by associating the ID of the terminal device 1 and search time data and including them in the user data. Here, the search time data represents a timing (time) at which the notification communication packet was received when the terminal device was retrieved. The communication control unit 64 may further include positional data of the terminal device 1 in the user data. The communication control unit 64 transmits the user data stored in the data storage 65 to the server apparatus 3 by controlling the third communication unit 63. In one embodiment, the communication control unit 64 may transmit the user data to the server apparatus 3, every time user data is stored in the data storage 65. The operation is not limited thereto, and, for example, in other embodiment, the communication control unit 64 may transmit user data stored in the data storage 65 to the server apparatus 3 at a specific timing (for example, at a regular timing or periodical timing). For example, when the size of user data stored in the data storage 65 exceeds a specific threshold, the communication control unit 64 may transmit the user data to the server apparatus 3.

In one embodiment, when an SOS flag included in a notification communication packet received from the terminal device 1 is set to "on", in other words, when the user of the terminal device 1 indicates urgent situation (a degree of urgency is high), the communication control unit 64 may transmit such user data to the server apparatus 3 with priority (with priority higher than transmission of other data).

The communication control unit 64 determines whether or not information representing "presence" of uploading request exists in an upload request flag included in a notification communication packet which is received, during a specific scanning period, from one or more terminal devices 1. When information representing that such "presence" of uploading request is set in the upload request flag, the communication control unit 64 records the ID included in the notification communication packet into transmission management data (transmission management information) stored in the data storage 65. Such addition of an ID to the transmission management data, for example, may be performed in order of reception of a notification communication packet. In such a case, the transmission management data recorded in one specific scanning period may be overwritten by transmission management data recorded at the time in a later scanning period after the one scanning period.

FIG. 10 illustrates one example of the data configuration of transmission management data recorded by the communication control unit 64. In this example, data records including a number of retrieving during a scanning period and the ID may be recorded in the transmission management data, according to an order of reception of notification communication packets. The data configuration illustrated in FIG. 10 is one specific example. As the configuration of the transmission management data, other forms such as a table, a list, or a database may be used.

The communication control unit 64, for example, may load IDs and data records being recorded in the transmission management data from the data storage 65 in order of searching, for each scanning period. The communication control unit 64 controls the second communication unit 62 to execute a second reception process for a terminal device 1 identified by the ID included in the data record. The communication control unit 64, for example, may control to repeat the second reception process described above by loading data records included in the transmission management data in order of the "NUMBER" (for example, as shown in FIG. 10).

When reception of transmission data from certain terminal device 1 has been completed successfully by the second reception process, the communication control unit 64 may delete the data record including the ID corresponding to the certain terminal device 1, from the transmission management data. The communication control unit 64 may control the second communication unit 62 to execute the second reception process for another terminal device 1 which is identified by an ID recorded in the data record being stored next to the deleted ID corresponding to the certain terminal device 1.

On the other hand, for example, when reception of transmission data has been failed due to a communication error, a timeout, or the like, the communication control unit 64 may control to execute the second reception process for the next terminal device 1 without retrying, or after a certain number of retrying. By these processes, the communication control unit 64 may evenly assign triggers for executing the second reception process over time to each of the terminal devices 1 of which IDs are recorded in the transmission management data. Then, the communication control unit 64 stores transmission data received through the second reception process in the data storage 65 by associating with an ID of the terminal device 1.

In addition, the communication control unit 64 transmits transmission data stored in the data storage 65 to the server apparatus 3 in association with the ID of the terminal device 1, for each scanning period, by controlling the third communication unit 63. The communication control unit 64 may transmit transmission data received from certain terminal device prior to other transmission data (e.g. with priority over transmission of other data), when an SOS flag included in a notification communication packet received from the certain terminal device 1 is set to "on". In other words, in a case of high urgency is notified from the user of the certain terminal device 1, the communication control unit 64 may transmit transmission data corresponding to the certain terminal device 1 to the server apparatus 3 with priority (with priority over transmission of other data).

Figure 11:
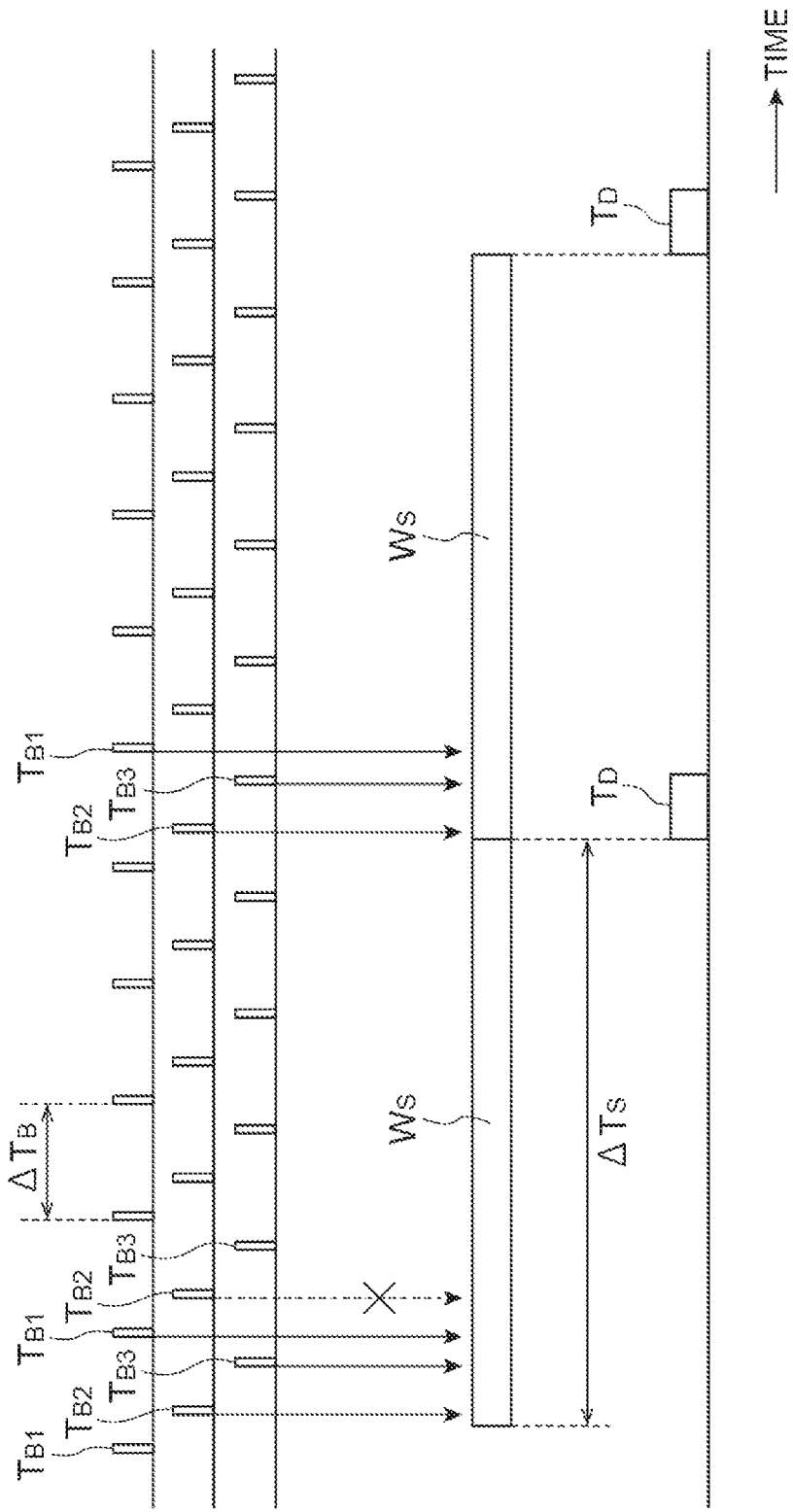
FIG. 11 is a timing diagram illustrating timings of a first reception process and a second reception process controlled by a communication control unit 64 of the gateway device 2.

FIG. 11 is a timing diagram illustrating timings of the first reception process and the second reception process controlled by the communication control unit 64. During a scanning period $W_S$ of which duration is set to $\Delta T_S$, a plurality of terminal devices 1 transmit notification communication packets at timings $T_{B1}$, $T_{B2}$, and $T_{B3}$ at transmission intervals $\Delta T_B$, and in accordance with the first reception process, the gateway device 2 is able to retrieve (detect) these user terminals 1. For each retrieved terminal device 1, the gateway device 2 may acquire the notification communication packet that has firstly been received, and then accordingly execute the process of transmitting user data generated in those user devices 1. In addition, the gateway device 2 may discard notification communication packets transmitted from the same terminal device 1 after the first notification communication packet in a specific scanning period $W_S$.

In addition, in a period $T_D$ after a specific scanning period $W_S$, the gateway device 2 can execute the second reception process for the plurality of terminal devices 1 retrieved in the scanning period $W_S$ and the process of transmitting, to other devices, transmission data relating to such plurality of terminal devices.

Under such control of the communication control unit 64, while the second communication unit 62 is occupied by the second reception process, the first reception process using the first communication unit 61 is able to be executed in parallel. By this implementation, the gateway device 2 is able to receive, by the first communication unit 61, notification communication packets from a plurality of terminal devices 1 other than the terminal device 1 from which transmission data is being received in accordance with the second reception process.

Figure 12:
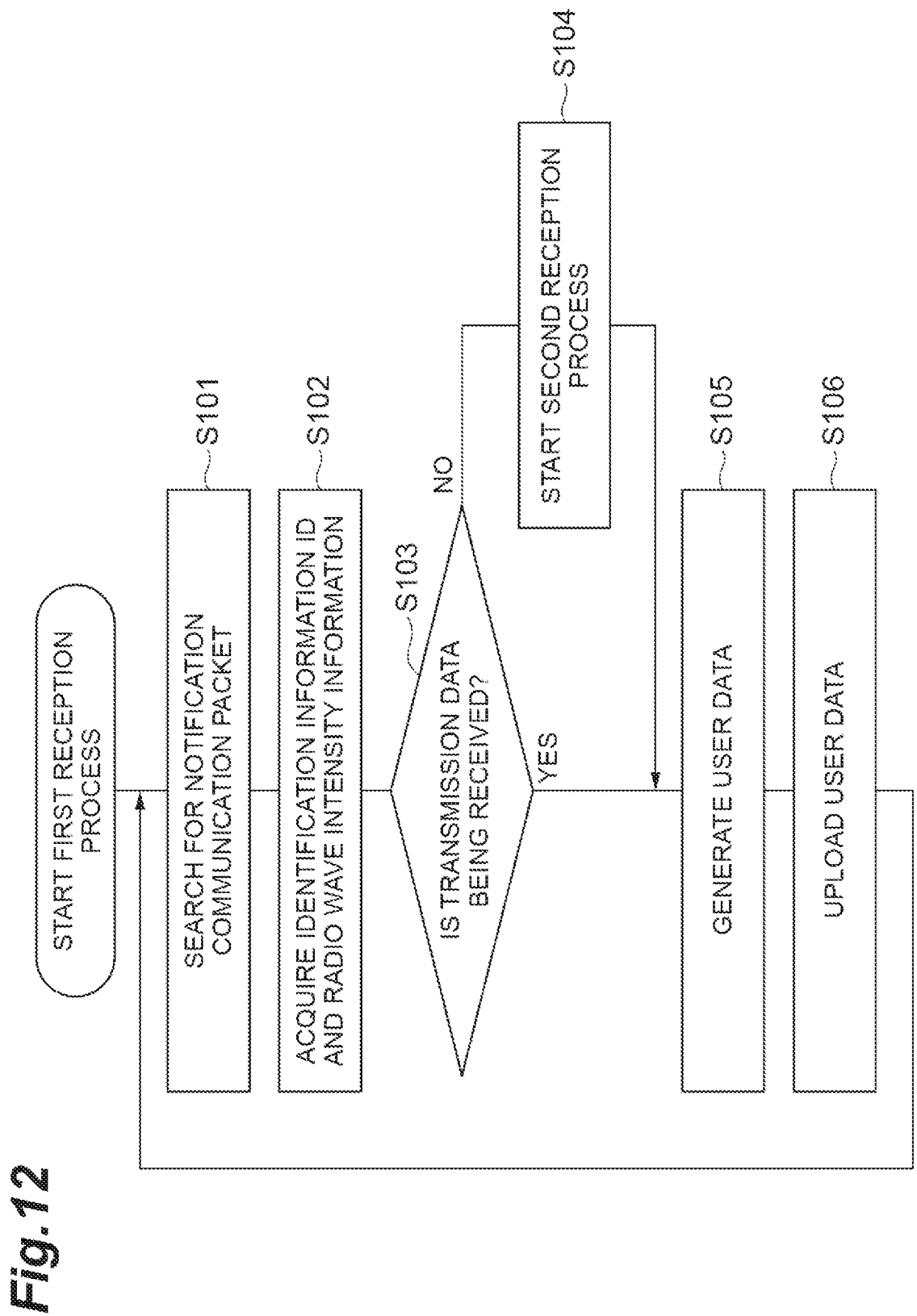
FIG. 12 is a flowchart illustrating the sequence of the first reception process and a transmission process according thereto in the communication system 100.
Figure 13:
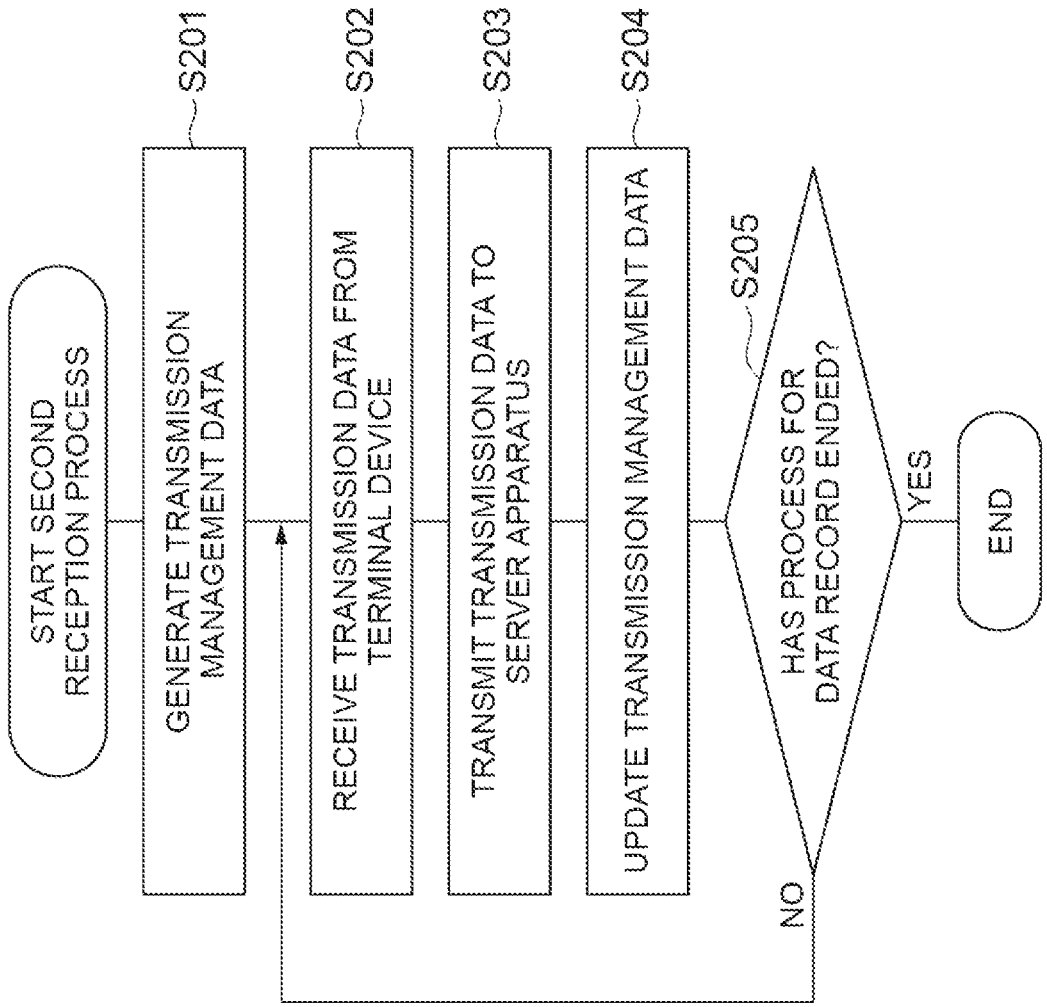
FIG. 13 is a flowchart illustrating the sequence of the second reception process and a transmission process according thereto in the communication system 100.

The processing of the communication system 100 and a communication method according to this embodiment will be described in detail by referring to FIG. 12 and FIG. 13. FIG. 12 is a flowchart illustrating a first reception process and related transmission process in the gateway device 2 of the communication system 100, and FIG. 13 is a flowchart illustrating a second reception process and related transmission process in the gateway device 2 of the communication system 100. The flowcharts illustrated in FIGS. 12 and 13 represent one specific example, and technologies according to this embodiment are not limited thereto. One or more part of the processes (steps) configuring each flowchart may be executed in parallel or may be executed by different order of sequences, when it does not affect the result.

The process illustrated in FIG. 12, for example, may be repeatedly executed for each of a plurality of terminal devices 1. By receiving notification communication packets from the terminal devices 1, the gateway device 2 searches for a terminal device 1 close to the gateway device 2 (Step S101). The gateway device 2 acquires information regarding IDs included in the received notification communication packets and radio wave intensities at the time of receiving the packets (Step S102).

The gateway device 2 determines whether reception of transmission data according to the second reception process is being executed (Step S103). When the gateway device 2 determines that the second reception process is not executed (Step S103: No), the gateway device 2 starts the second reception process on a timing of the end of each scanning period (Step S104).

The gateway device 2 generates user data on the basis of the information of the ID and the radio wave intensities that have been acquired from user terminal 1 (Step S105). The gateway device 2 transmits (uploads) the generated user data to the server apparatus 3 (Step S106). The gateway device 2, for example, may transmit user data to the server apparatus 3 every time the user data is generated.

Then, the gateway device 2 may repeatedly execute a search for other terminal devices 1 (Step S101).

The second reception process will be described with reference to FIG. 13.

The gateway device 2 generates transmission management data on the basis of IDs of one or more terminal devices 1 retrieved in a scanning period (Step S201).

The gateway device 2 sequentially loads data records from the generated transmission management data and, receives transmission data from a terminal device 1 identified in the loaded data record (Step S202).

The gateway device 2 transmits the transmission data received from the terminal device 1 and the ID to the server apparatus 3 by associating them (Step S203). The gateway device 2 determines whether reception process and transmission process of the transmission data have been successfully completed. When reception and transmission process of the transmission data have been completed successfully, the gateway device 2 may delete the data record relating to the terminal device 1 which is transmission source of the transmission data being successfully transmitted (Step S204). In this way, the transmission management data is updated.

The gateway device 2 determines whether or not the second reception process relating to all of the data records in the transmission management data has been executed (Step S205). When the second reception process relating to one or more data records has not been executed (Step S205; No), the gateway device 2 may restart the process from Step S202. On the other hand, when the second reception process relating to all the data records has been executed (Step S205; Yes), the gateway device 2 may finish the second reception process.

The gateway device 2 according to this embodiment is able to continuously collect biomedical information without omission from one or more terminal devices 1 having biomedical information to be collected, among terminal devices 1 that have transmitted notification signals. As a result, the gateway device 2 is able to efficiently collect data including biomedical information from terminal devices 1.

Such a gateway device 2 is able to execute the first process of receiving notification communication packets including IDs and upload request flags from one or more terminal devices 1, and the second process of receiving transmission data including biomedical information from the terminal devices 1 in parallel. In addition, when information representing "presence" of uploading request is set in the upload request flag included in the notification communication packet, the gateway device 2 records the ID included in the notification communication packet into transmission management data. Then the gateway device 2 sequentially receives transmission data from a plurality of terminal devices 1 which are identified by the IDs recorded in the transmission management data. With this procedure, the gateway device 2 is able to continuously collect biomedical information without omission from one or more terminal devices 1 having biomedical information to be collected, among a plurality of terminal devices 1 that have transmitted notification communication packets. As a consequence, the gateway device 2 is able to collect data including biomedical information efficiently from terminal devices 1.

In this embodiment, in accordance with a received notification communication packet, the communication control unit 64 of the gateway device 2 estimates the position of a terminal device 1 that has transmitted the communication packet. In accordance with such a configuration, the gateway device 2 is able to collect data of estimated position of the terminal device 1.

In addition, the gateway device 2 (the communication control unit 64) is able to execute the first reception process in parallel with the second reception process, while the second communication unit 62 is occupied by the second reception process. For example, a case where the size of transmission data receivable by the second communication unit 62 is set to be larger than the size of data of a notification communication packet receivable by the first communication unit 6 can be assumed. Even in such case, the gateway device 2 is able to receive a notification communication packet from certain terminal device 1, while the second communication unit 62 is occupied by the second reception process for another terminal device 1. In other words, the gateway device 2 configured as above is able to receive a notification communication packet while receiving transmission data. Therefore, the gateway device 2 is able to collect necessary data, from a plurality of terminal devices 1 having biomedical information to be collected, efficiently and continuously.

The gateway device 2 (the communication control unit 64) may wait for a notification communication packet during a scanning period in which a notification communication packet is transmitted by the terminal device 1, in the first reception process. The gateway device 2 records the ID included in the notification communication packet received during the scanning period, into the transmission management data. With such a configuration, the gateway device 2 is able to regularly search for the terminal device 1 that is a candidate for the second reception process and to efficiently collect data from one or more terminal devices 1, in accordance with a size of transmission data and an update period.

The scanning period may be set to be longer than a transmission interval of notification communication packets in the terminal devices 1. With such a setting, the gateway device 2 is able to collect data from a plurality of terminal devices 1 more efficiently.

The gateway device 2 (the communication control unit 64) is able to evenly assign triggers to execute the second reception process over time for each of a plurality of terminal devices 1 of which IDs are recorded in the transmission management data. According to such a configuration, the gateway device 2 is able to collect data from a plurality of terminal devices 1 without omission.

In addition, the gateway device 2 (the communication control unit 64) is able to set the size of transmission data received from a plurality of terminal devices 1 to a specific size for each terminal device 1 in the second reception process. In other words, the gateway device 2 is able to limit the size of transmission data for each terminal device 1. In accordance with this, the gateway device 2 is able to reduce a delay regarding reception of transmission data from one terminal device 1 caused by reception of transmission data from another terminal device 1. In this way, the gateway device 2, for example, is able to timely collect data from terminal devices 1 without omission.

The gateway device 2 (the communication control unit 64) may delete, from the transmission management data, the ID to identify the terminal device 1 from which transmission data of a specific size has been received. Then, the gateway device 2 may receive transmission data from the terminal device 1 other than the terminal device 1 of which ID is deleted from the transmission management data. In accordance with such a configuration, the gateway device 2 can change the terminal device from which transmission data are collected (received), among terminal devices 1 having biomedical information to be collected, without overlapping. In this case, the gateway device 2 is able to collect data from terminal devices 1 without deviation.

The gateway device 2 (the communication control unit 64) may append IDs in received notification communication packets into the transmission management data, in order of reception of those notification communication packets during the second reception process. Then, the gateway device 2 may repeat the process of sequentially loading IDs recorded in the transmission management data and receiving transmission data from a terminal device 1 identified by each of the loaded IDs. In accordance with such a configuration, the gateway device 2 is able to sequentially switch the terminal device 1 from which transmission data is received, among a plurality of terminal devices 1 having biomedical information to be collected. In this way, the gateway device 2 is able to collect data from the plurality of terminal devices 1 without omission.

The gateway device 2 (the communication control unit 64) may overwrite, in the transmission management data, the IDs included in notification communication packets received during certain scanning period, with the IDs included in notification communication packets received during later scanning period after the certain scanning period. By this, the gateway device 2 is able to repeatedly execute process of receiving transmission data for every scanning period, for each of terminal devices 1 having biomedical information to be collected. In this case, the gateway device 2 is able to efficiently collect data from terminal devices 1 in accordance with the size of transmission data and an update period.

The gateway device 2 according to one embodiment, as described above, may further include the third communication unit 63 that is configured to transmit data to the server apparatus 3 through a communication line. In the gateway device 2, the communication control unit 64 transmits, to the server apparatus 3 by controlling the third communication unit 63, the ID in the notification communication packet received by the first communication unit 61 and transmission data received by the second communication unit 62. In accordance with such a configuration, the gateway device 2 can transmit transmission data received from terminal devices 1 to the server apparatus 3 together with the ID of each of the terminal devices 1. In this way, the gateway device 2 enables the server apparatus 3 to continuously collect biomedical information from terminal devices 1 without omission.

In one embodiment, when specific information representing urgent situation (degree of urgency is high) relating to a terminal device 1 is included in a notification communication packet received from a terminal device 1, the gateway device 2 transmits the ID in the notification communication packet received from such terminal device 1 to the server apparatus 3 with priority. More specifically, the communication control unit 64 of the gateway device 2 executes such transmission with higher priority than other transmissions, by controlling the third communication unit 63. In accordance with such a configuration, the gateway device 2 enables to prioritize collection on the server apparatus 3 of information from the user's terminal device 1 with higher degree of urgency.

In one embodiment, the gateway device 2 (the communication control unit 64) may estimate a relational position between the terminal device 1 and the gateway device 2 itself on the basis of a notification communication packet received from the terminal device 1. Then, the gateway device 2 transmits, to the server apparatus 3, a timing at which the notification communication packet has been received from the terminal device 1 and data representing the estimated positional relation. In accordance with such a configuration, the gateway device 2 is able to transmit data representing the estimated relational position of the terminal device 1, and data representing time information (in this case, the timing of receiving the packet) to the server apparatus 3. In this case, the server apparatus 3, for example, is able to specify positions of a plurality of terminal devices 1 at certain timing.

In one embodiment, each of the first communication unit 61 and the second communication unit 62 of the gateway device 2 may be communicatively connected to the terminal device 1 through a radio communication channel. In this case, the communication control unit 64 of the gateway device 2 is able to identify a distance between the terminal device 1 and the gateway device 2 itself in accordance with a radio wave intensity of a radio communication channel, when the first communication unit 61 receives a notification communication packet from the terminal device 1 through the radio communication channel. More specifically, the communication control unit 64 of the gateway device 2 is able to identify such a distance, for example, by comparing the radio wave intensity with a threshold set in advance. In accordance with such a configuration, the gateway device 2 is able to estimate the position of the terminal device 1 with a simple computation.

The embodiment described above is not limited to the form described above, and various modifications and addition of functions can be acceptable.

For example, when reception of transmission data from certain terminal device 1 has been successfully completed, the communication control unit 64 of the gateway device 2 may set the data record corresponding to the certain terminal device 1 as last data in the transmission management data. Alternatively, the communication control unit 64 may repeatedly execute the second reception process by cyclically loading data records recorded in the transmission management data (such as a round robin system). In such case, triggers for the second reception process for a plurality of terminal devices 1 may also be evenly assigned over time.

In one embodiment, when the data amount of transmission data is predictable from a notification communication packet or the like received from a terminal device 1, the communication control unit 64 may control to receive smaller transmission data first. By such control, the gateway device 2 is able to improve the efficiency of collection and transmission of transmission data from terminal devices 1.

In one embodiment, a priority level may be set for each type of biomedical information included in transmission data. In such a case, the communication control unit 64 of the gateway device 2 may identify the terminal device 1 having biomedical information with a higher priority level from the notification communication packet received from the terminal device 1. Then, the gateway device 2 may receive transmission data from such identified terminal device 1 first. By performing such control, the gateway device 2 is able to collect transmission data with higher priority level from terminal devices 1 efficiently and effectively.

In one embodiment, the communication control unit 64 of the gateway device 2 may select, among a plurality of terminal devices 1, the particular terminal device 1 from which transmission data is received, in accordance with relational position between the gateway device 2 and each of the plurality of terminal devices 1. For example, the communication control unit 64 may select the terminal device 1 to which distance from the gateway device 2 itself is equal to or smaller than a specific distance and may determine to receive transmission data from the selected terminal device 1. When the gateway device 2 receives transmission data from the terminal device 1 through a radio communication channel, a data transmission speed, an error occurrence rate, and the like may be affected by a distance between the gateway device 2 and the terminal device 1. In other words, in a specific situation, the efficiency of communication may be improved by receiving transmission data from one terminal device 1 disposed at a relatively short distance than receiving transmission data from another terminal device disposed at a relatively long distance. In accordance with the configuration, the gateway device 2 is able to efficiently collect transmission data from a plurality of terminal devices 1 by selecting the terminal device 1 from which transmission data is received based on relational positions for each of the plurality of terminal devices 1.

In some embodiments, in the communication system 100, positional data relating to a plurality of terminal devices 1 may be shared among a plurality of gateway devices 2. In such a case, each of the gateway devices 2 is able to identify the terminal device 1 that is closer to the gateway device 2 than gateway devices 2 other than the gateway device 2 on the basis of the shared positional data. Each of the gateway devices 2 may receive transmission data from the terminal device 1 identified in this way. Gateway devices 2 may share the positional data by gateway devices 2 directly exchanging the positional data with each other through communication lines. Alternatively, those positional data may be collected on another device such as the server apparatus 3 from the plurality of gateway devices 2, and then distributed to gateway devices 2 again. In accordance with such a configuration, the gateway device 2 close to a terminal device 1 receives transmission data from the terminal device 1, and therefore, the communication system 100 is able to efficiently collect transmission data from a plurality of terminal devices 1.

The hardware configurations of the terminal device 1 and the gateway device 2 described in the embodiment described above are not limited to the configurations illustrated in FIGS. 4 and 7 described above. In other words, each of the terminal device 1 and the gateway device 2 may be realized by a combination of one or more dedicated hardware devices (integrated circuits and the like) or may be realized by a combination of general-purpose hardware devices and software programs. Such a software program may be introduced into the terminal device 1 and the gateway device 2 through a communication network or various recording media (an optical recording medium, a magnetic recording medium, a flash memory, and the like).

The technologies relating to the present disclosure have been described using embodiment as described above. The technologies relating to the present disclosure are not limited to each embodiment described above, and variations, various alterations and modifications within the scope of the technical idea can be made. In addition, a combination of each embodiment described above, and variations and a combination of modifications or modified forms thereof also belong to the technical scope relating to the present disclosure.

What is claimed is:

1. A communication device comprising:
   a first communication circuit configured to receive, from, notification signals including user terminal identification information and a transmission request to provide transmission data including biomedical information re of a user;
   a second communication circuit configured to receive the transmission data, a size of the transmission data being larger than a size of data of the notification signals; and
   a controller configured to:
      receive a first notification signal from a first user terminal using the first communication circuit;
      determine to receive the transmission data from the first user terminal when the transmission request information in the first notification signal represents that biomedical information to be transmitted of a user of the first user terminal is recorded in the first user terminal; and execute, in parallel, a first process of receiving a second notification signal from a second user terminal by controlling the first communication circuit and a second process of receiving the transmission data from the first user terminal by controlling the second communication circuit.

2. The communication device according to claim 1, further comprising a memory configured to store data, wherein the controller is further configured to,
on determining to receive the transmission data from specific the first user terminal, record the user terminal identification information included in the first notification signal into transmission management information stored in the memory and configured to include at least one record representing the user terminal identification information, and
when one or more user terminal identification information is recorded in the transmission management information, execute sequentially the second process for user terminals identified by each of the user terminal identification information recorded in the transmission management information, by controlling the second communication circuit.

3. The communication device according to claim 1, wherein the controller is further configured to estimate a position of the first user terminal in accordance with the first notification signal.

4. The communication device according to claim 2, wherein the controller is further configured to wait for the second notification signal during a scanning period set as a duration to receive the first notification signal in the first process, and
record the user terminal identification information included in the first notification signal into the transmission management information.

5. The communication device according to claim 4, wherein the scanning period is set to be longer than a transmission interval of the first notification signal in the first user terminal.

6. The communication device according to claim 1, wherein the controller is further configured to evenly assigns triggers for executing the second process for each of the user terminals of which user terminal identification information is recorded in the transmission management information.

7. The communication device according to claim 1, wherein the controller is further configured to, in the second process, limit a size of the transmission data receiving at once from the user terminals to a specific size for each of the user terminals.

8. The communication device according to claim 7, wherein the controller is further configured to
delete, from the transmission management information, user terminal identification information indicating a user terminal from which the transmission data of a specific size has been received, and
receive the transmission data from another user terminal among user terminals identified by the user terminal identification information remaining in the transmission management information.

9. The communication device according to claim 2, wherein the controller is further configured to append the user terminal identification information included in the notification signals to the transmission management information in order of reception of the notification signals, and
in the second process, sequentially read the user terminal identification information recorded in the transmission management information and receive the transmission data from the user terminal identified by the read user terminal identification information.

10. The communication device according to claim 4, wherein the controller is further configured to
overwrite transmission management information by replacing the user terminal identification information included in the notification signal received during certain scanning period, with other user terminal identification information included in the notification signal received during the scanning period later than the certain scanning period.

11. The communication device according to claim 1, further comprising a third communication circuit configured to transmit data to another device through a communication line, and wherein the controller is further configured to transmit the user terminal identification information included in the first notification signal and the transmission data to the other device by controlling the third communication circuit.

12. The communication device according to claim 11, wherein, the controller is further configured to when information representing an urgent state is included in the first notification signal, transmit the user terminal identification information included in the first notification signal including the information representing the urgent state, to the other device with higher priority than transmission of other user terminal identification information, by controlling the third communication circuit.

13. The communication device according to claim 11, wherein the controller further is configured to
estimate a relative position between the first user terminal and the communication device based on the first notification signal, and
transmit data including a timing at which the first notification signal is received and the relative position between the first user terminal and the communication device to the other device by controlling the third communication circuit.

14. The communication device according to claim 13, wherein each of the first communication circuit and the second communication circuit is further configured to establish communication connection to the first user terminal via a radio communication channel, and
the controller identifies a distance between the first user terminal and the communication device in accordance with a signal intensity of the radio communication channel when the first communication circuit receives the first notification signal through the radio communication channel.

15. The communication device according to claim 14, wherein the controller is further configured to identify the distance by comparing the signal intensity with a threshold set in advance.

16. A communication system comprising:
the communication device according to claim 1; and
the first user terminal;
the second user terminal.

17. The communication system according to claim 16, wherein the communication device selects one of the user terminals, to receive the transmission data in accordance with relative positions between the communication device and each of the user terminals.

18. The communication system according to claim 16, wherein the communication device selects one of the user terminals, to receive the transmission data in accordance with relative position between the communication device and each of the user terminals, further comprising a plurality of the communication devices according to claim 1, wherein each of the plurality of the communication devices
- estimates relative position for each of the user terminals,
- shares the estimated relative positions among the plurality of the communication devices by communicating with each other,
- selects a closest user terminal to itself, based on the shared relative positions, and
- receives the transmission data from the selected user terminal.

19. A communication method executed by a communication device, the communication method comprising:
- receiving a first notification signal from a first user terminal, the first notification signal including user terminal identification information and a transmission request to provide transmission data including biomedical information of a user of the first user terminal;
- determining to receive the transmission data from the first user terminal, when the transmission request represents that the biomedical information to be transmitted is recorded in the first user terminal; and
- executing, in parallel, a first process of receiving a second notification signal from a second user terminal and a second process of receiving the transmission data from the first user terminal,
- wherein a size of the transmission data is larger than a size of data of the first notification signal and a size of data of the second notification signal.

* * * * *